(12) United States Patent
Patton

(10) Patent No.: US 11,806,436 B1
(45) Date of Patent: Nov. 7, 2023

(54) DOOR HANDLE SANITIZER

(71) Applicant: Precious Patton, Hampton, VA (US)

(72) Inventor: Precious Patton, Hampton, VA (US)

(*) Notice: Subject to any disclaimer, the term of this patent is extended or adjusted under 35 U.S.C. 154(b) by 554 days.

(21) Appl. No.: 17/093,762

(22) Filed: Nov. 10, 2020

(51) Int. Cl.
A61L 2/18 (2006.01)
G08C 17/04 (2006.01)
B05B 15/68 (2018.01)
A61L 2/26 (2006.01)
A61L 2/24 (2006.01)
A61L 101/44 (2006.01)

(52) U.S. Cl.
CPC .......... A61L 2/18 (2013.01); A61L 2/24 (2013.01); A61L 2/26 (2013.01); B05B 15/68 (2018.02); G08C 17/04 (2013.01); A61L 2101/44 (2020.08); A61L 2202/11 (2013.01); A61L 2202/14 (2013.01); A61L 2202/15 (2013.01)

(58) Field of Classification Search
CPC ..... A61L 2/18; A61L 2/24; A61L 2/26; A61L 2202/14; A61L 2202/15; A61L 2202/20; E05B 1/0069
See application file for complete search history.

(56) References Cited

U.S. PATENT DOCUMENTS

| 5,314,668 | A | 5/1994 | Biermaier |
| 6,789,695 | B1 | 9/2004 | Gaudreau |
| 6,874,697 | B2 | 4/2005 | Callueng |
| 7,320,418 | B2 | 1/2008 | Sassoon |
| D670,552 | S | 11/2012 | Meeks |
| 2010/0147974 | A1 | 6/2010 | Cunningham |
| 2018/0135332 | A1 | 5/2018 | Conlan |

FOREIGN PATENT DOCUMENTS

WO 2006074454 7/2006

Primary Examiner — Lessanework Seifu
(74) Attorney, Agent, or Firm — Kyle A. Fletcher, Esq.

(57) ABSTRACT

The door handle sanitizer is an electromechanical device. The door handle sanitizer is configured for use with a door. The door further comprises a door handle. The door handle sanitizer sprays a disinfecting solution on the door handle such that the disinfecting solution disinfects the door handle of pathogens, including viruses such as COVID-19. The door handle sanitizer comprises a track structure and a disinfection structure. The track structure attaches the disinfection structure to the door. The track structure is a flexible structure that forms a path that guides the disinfection structure around the door handle. The disinfection structure moves along the path formed by the track structure such that the disinfection structure has access to all surfaces of the door handle. The disinfection structure discharges the disinfection solution on the door handle.

20 Claims, 8 Drawing Sheets

CAS 8001-54-5

CAS 2893-78-9

DOOR HANDLE SANITIZER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of doors and locks including door handles, more specifically, a disinfecting structure for a door handle. (E05B1/0069)

SUMMARY OF INVENTION

The door handle sanitizer is an electromechanical device. The door handle sanitizer is configured for use with a door. The door further comprises a door handle. The door handle sanitizer sprays a disinfecting solution on the door handle such that the disinfecting solution disinfects the door handle of pathogens, including viruses such as COVID-19. The door handle sanitizer comprises a track structure and a disinfection structure. The track structure attaches the disinfection structure to the door. The track structure is a flexible structure that forms a path that guides the disinfection structure around the door handle. The disinfection structure moves along the path formed by the track structure such that the disinfection structure has access to all surfaces of the door handle. The disinfection structure discharges the disinfection solution on the door handle.

These together with additional objects, features and advantages of the door handle sanitizer will be readily apparent to those of ordinary skill in the art upon reading the following detailed description of the presently preferred, but nonetheless illustrative, embodiments when taken in conjunction with the accompanying drawings.

In this respect, before explaining the current embodiments of the door handle sanitizer in detail, it is to be understood that the door handle sanitizer is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the door handle sanitizer.

It is therefore important that the claims be regarded as including such equivalent construction insofar as they do not depart from the spirit and scope of the door handle sanitizer. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
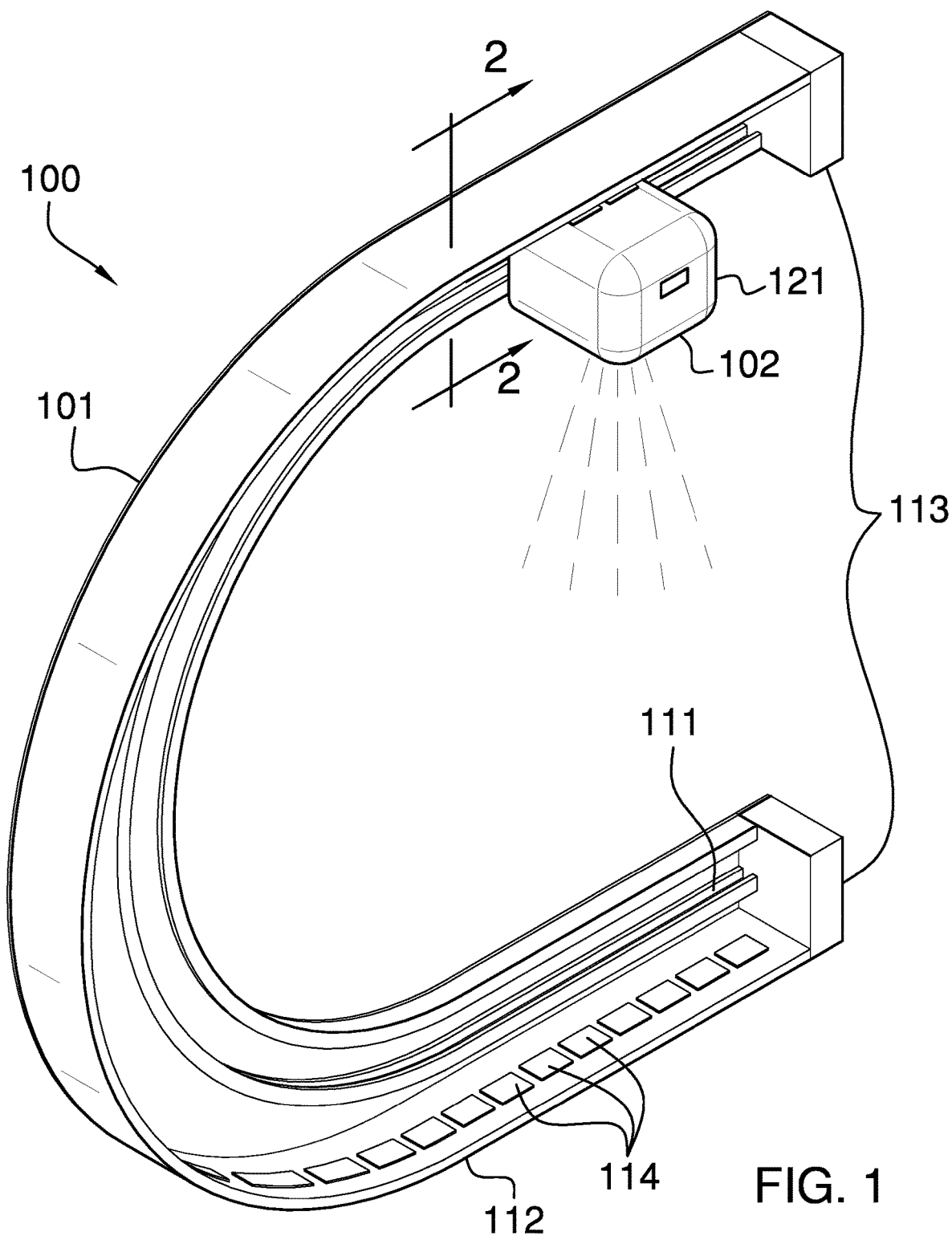
FIG. 1 is a perspective view of an embodiment of the disclosure.
Figure 2:
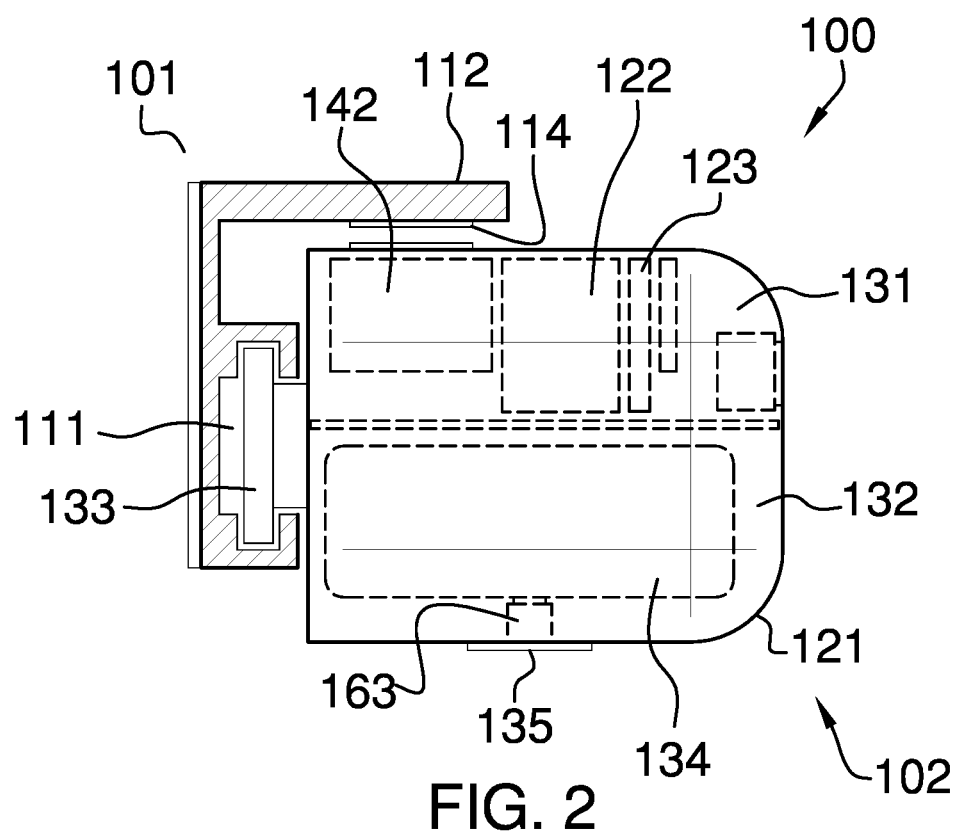
FIG. 2 is a side view of an embodiment of the disclosure.
Figure 3:
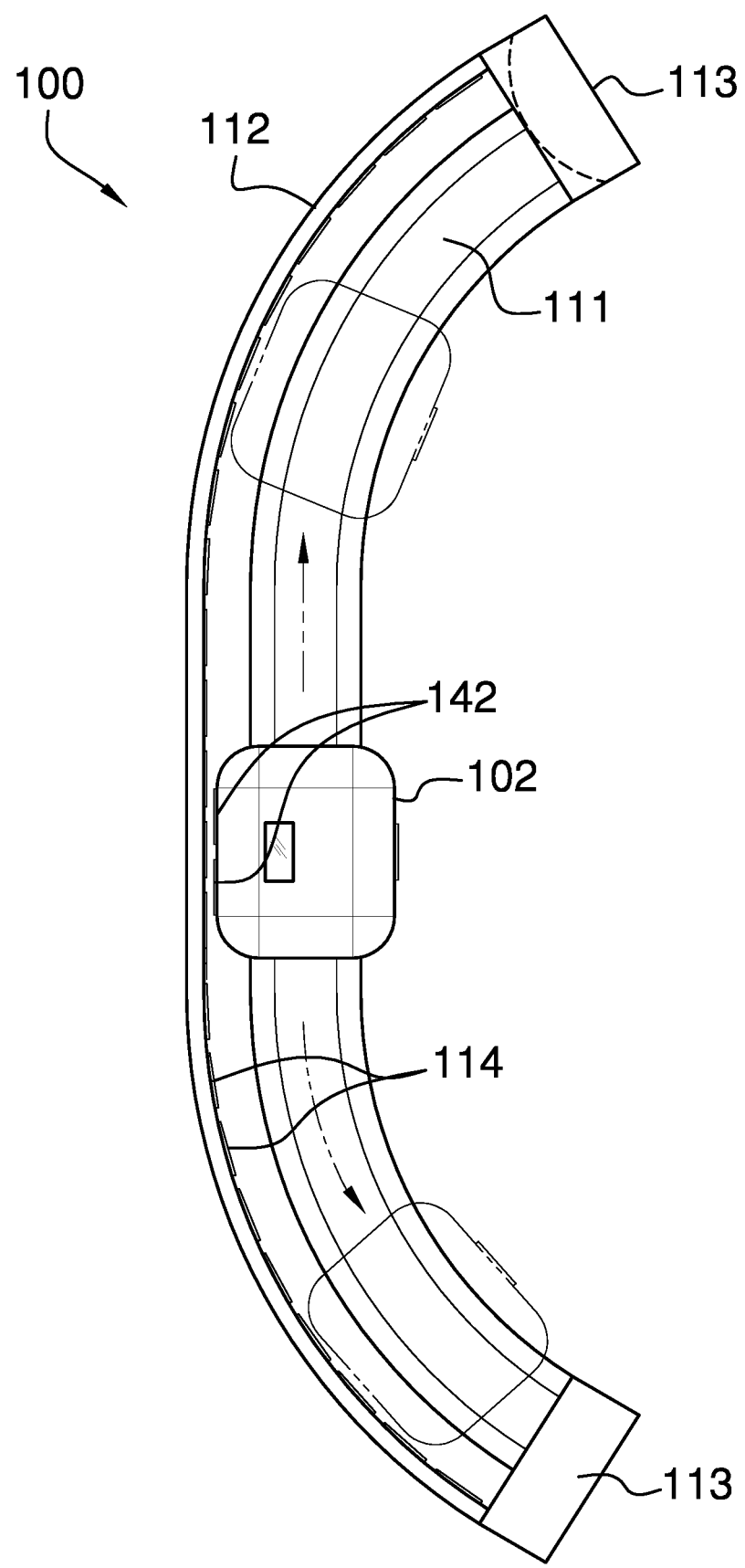
FIG. 3 is a front view of an embodiment of the disclosure.
Figure 4:
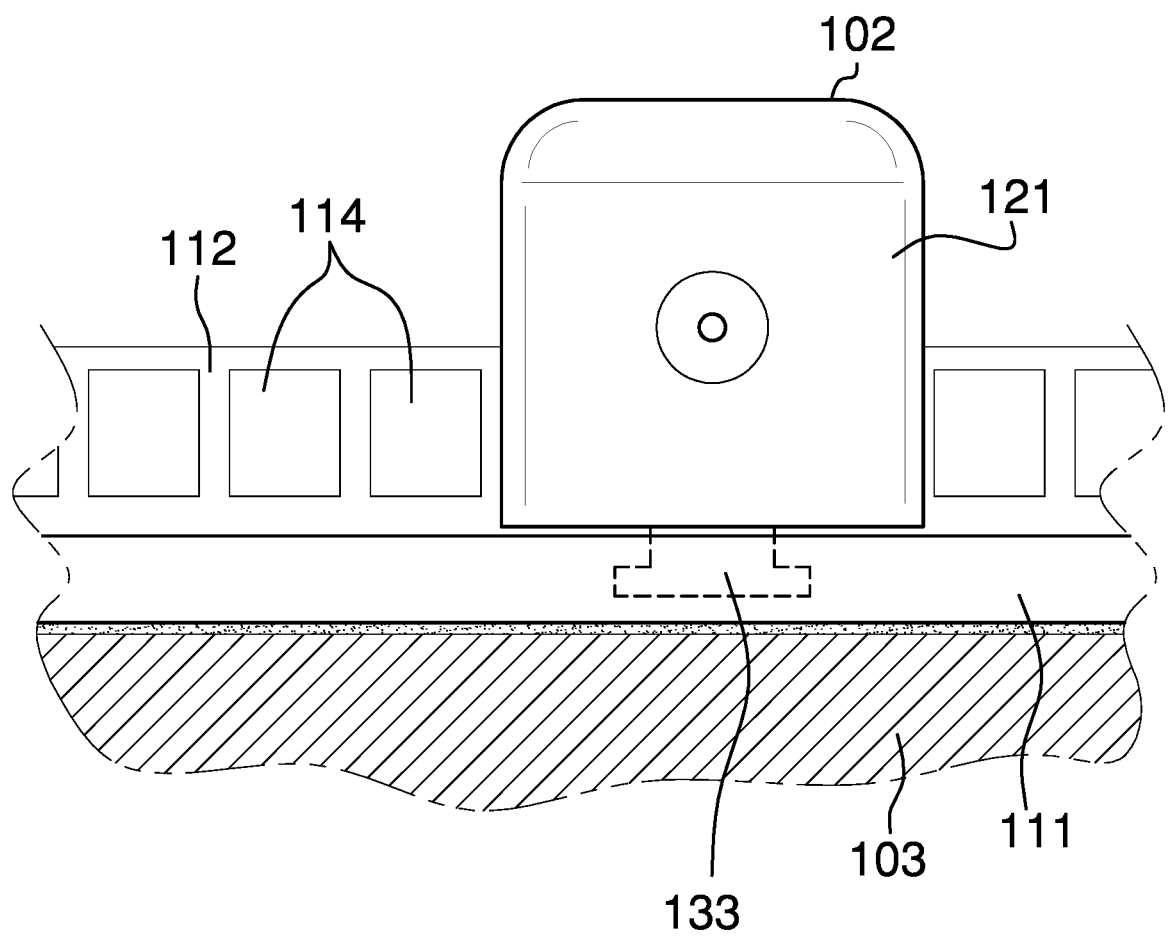
FIG. 4 is a bottom view of an embodiment of the disclosure.
Figure 5:
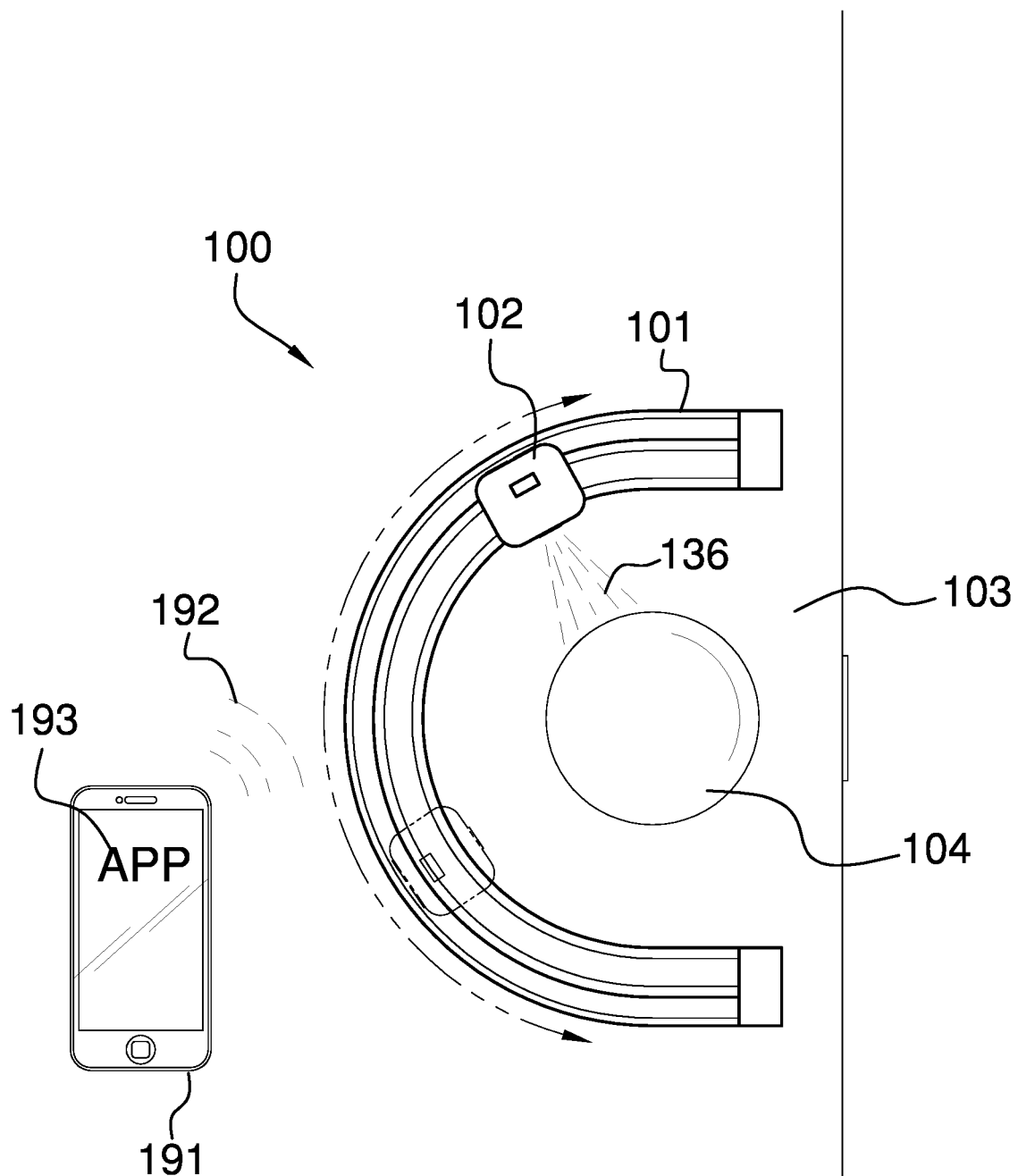
FIG. 5 is an in-use view of an embodiment of the disclosure.
Figure 6:
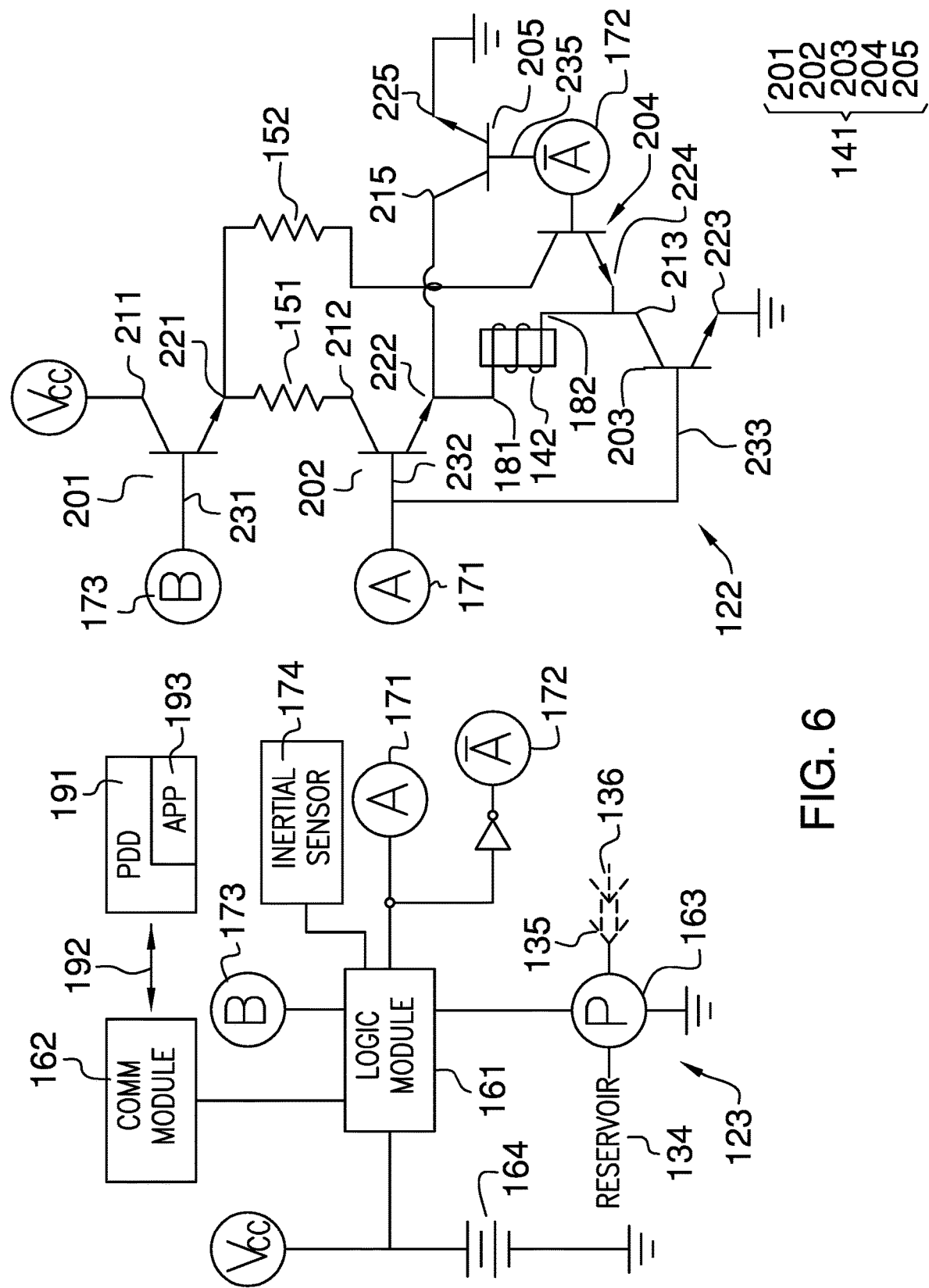
FIG. 6 is a schematic view of an embodiment of the disclosure.
Figure 7A:
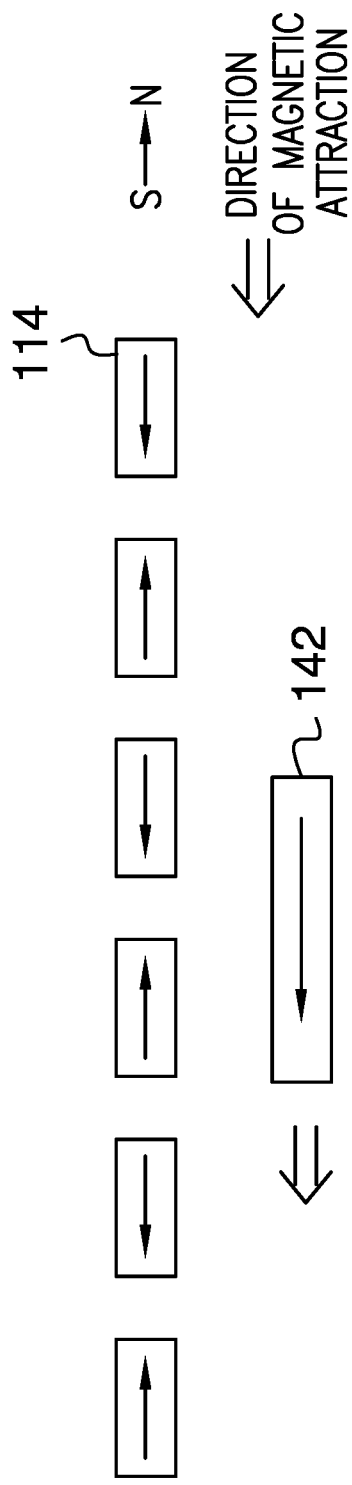
FIG. 7a is a detail view of an embodiment of the disclosure.
Figure 7B:
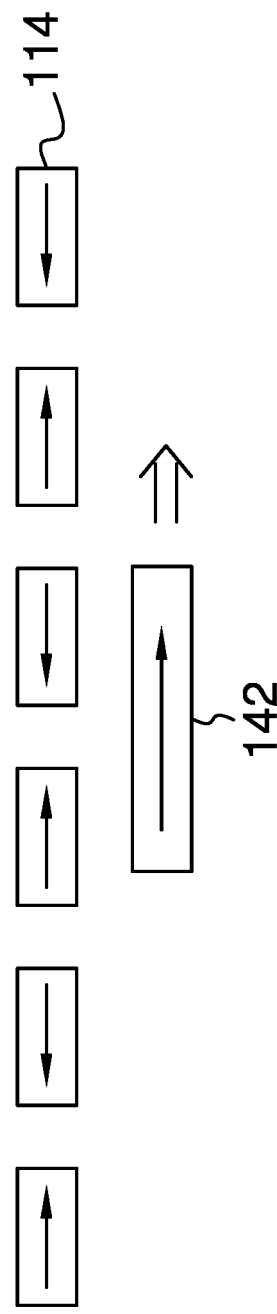
FIG. 7b is a detail view of an embodiment of the disclosure.
Figure 8:
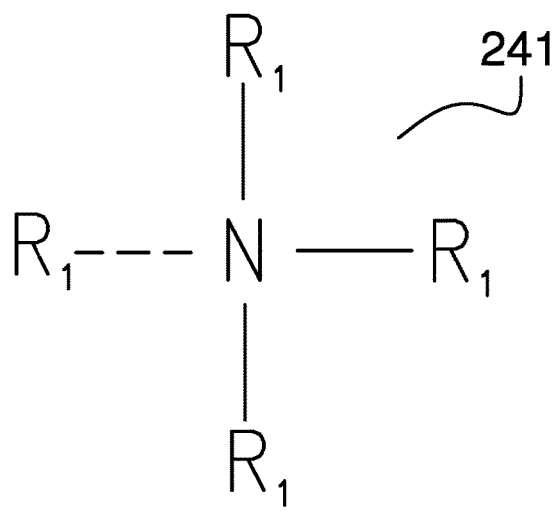
FIG. 8 is a detail view of an embodiment of the disclosure.
Figure 9:
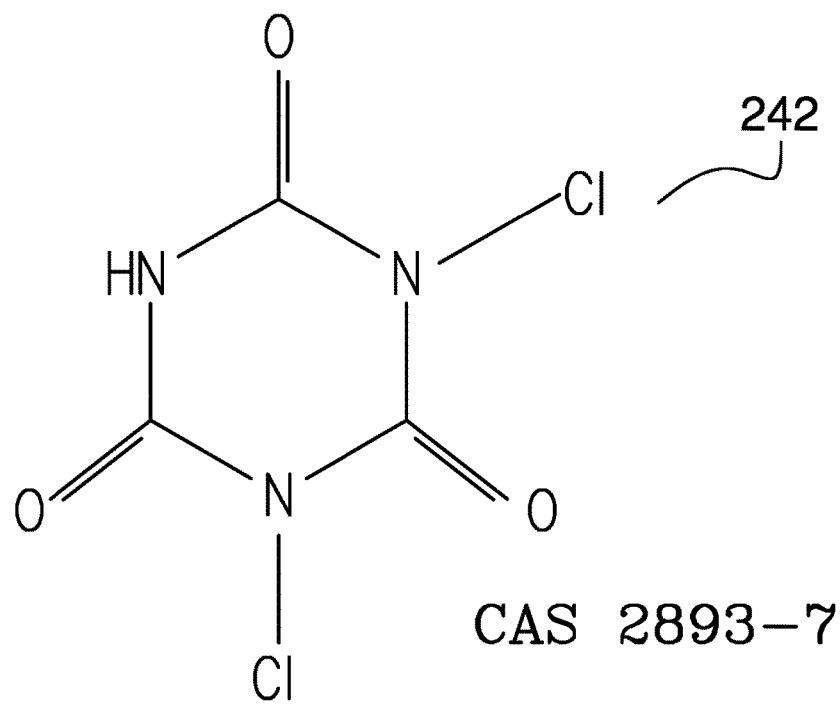
FIG. 9 is a detail view of an embodiment of the disclosure.

Detailed reference will now be made to one or more potential embodiments of the disclosure, which are illustrated in FIGS. 1 through 9.

The door handle sanitizer 100 (hereinafter invention) is an electromechanical device. The invention 100 is configured for use with a door 103. The door 103 further comprises a door 103 handle 104. The invention 100 sprays a disinfection solution 136 on the door 103 handle 104 such the disinfection solution 136 disinfects the door 103 handle 104 of pathogens including viruses such as COVID-19. The invention 100 comprises a track structure 101 and a disinfection structure 102. The track structure 101 attaches the disinfection structure 102 to the door 103. The track structure 101 is a flexible structure that forms a path that guides the disinfection structure 102 around the door 103 handle 104. The disinfection structure 102 moves along the path formed by the track structure 101 such that the disinfection structure 102 has access to all surfaces of the door 103 handle 104. The disinfection structure 102 discharges the disinfection solution 136 on the door 103 handle 104. The door 103 and the door 103 handle 104 are defined elsewhere in this disclosure.

The track structure 101 is a mechanical structure. The track structure 101 secures the disinfection structure 102 to the door 103. The track structure 101 is a bimodal flexible structure. The bimodal flexible structure is defined elsewhere in this disclosure. The bimodal flexible structure of the track structure 101 allows for the attachment of the track structure 101 to the door 103 with a curvature that allows the track structure 101 to enclose or partially enclose the door 103 handle 104. The track structure 101 forms a track that guides the disinfection structure 102 around the path that encloses or partially encloses the door 103 handle 104. The path formed by the track structure 101 provides the disinfection structure 102 with the access required to discharge the disinfection solution 136 directly onto all the surfaces of the door 103 handle 104.

The track structure 101 is a passive magnetic structure. The magnetic structure of the track structure 101 is aligned such that the track structure 101 supports an active magnetic propulsion structure formed by the disinfection structure 102.

The track structure 101 comprises a guide track 111, a magnet plate 112, a plurality of termination caps 113, and a plurality of stationary magnets 114. The plurality of stationary magnets 114 attach to the magnet plate 112. The magnet plate 112 and the plurality of termination caps 113 attach to the guide track 111.

The guide track 111 is a track. The track is defined elsewhere in this disclosure. The guide track 111 forms a negative space with a semi-enclosed non-Euclidean prism shape. The guide track 111 is sized to receive the tracking wheel 133 of the disinfection structure 102 such that the guide track 111 guides the motion of the tracking wheel 133. The guide track 111 is a bimodal flexible structure. The bimodal flexible structure is defined elsewhere in this disclosure. The bimodal flexible structure of the guide track 111 allows for the attachment of the guide track 111 to the door 103 with a curvature that allows the guide track 111 to enclose or partially enclose the door 103 handle 104. The guide track 111 forms a track that guides the disinfection structure 102 around the path that encloses or partially encloses the door 103 handle 104.

The magnet plate 112 is a flexible disk-shaped structure. The magnet plate 112 is a bimodal flexible structure. The bimodal flexible structure is defined elsewhere in this disclosure. The bimodal flexible structure of the magnet plate 112 allows for the attachment of the magnet plate 112 to the door 103 with a curvature that allows the magnet plate 112 to enclose or partially enclose the door 103 handle 104. The magnet plate 112 attaches to the guide track 111 such that the congruent ends of the disk structure of the magnet plate 112 bends to follow the center axis of the non-Euclidean prism structure of the guide track 111. Each of the plurality of stationary magnets 114 attaches to a congruent end of the disk structure of the magnet plate 112.

Each of the plurality of termination caps 113 is a bracing structure that attaches to a congruent end of the non-Euclidean prism structure of the guide track 111. The plurality of termination caps 113 forms a blocking structure that prevents the disinfection structure 102 from moving beyond the path formed by the guide track 111.

Each of the plurality of stationary magnets 114 is a permanent magnet. The plurality of stationary magnets 114 are arranged on the magnet plate 112 such that the plurality of stationary magnets 114 forms a plurality of alternating magnetic fields. By alternating magnetic fields is meant that any field directions of the magnetic fields generated by any two adjacent stationary magnets are reversed relative to each other. The plurality of stationary magnets 114 forms a passive magnetic field structure that interacts with an active magnetic field structure formed by the disinfection structure 102 to generate the motive forces necessary to move the disinfection structure 102 along the path formed by the guide track 111.

The disinfection structure 102 is an electromechanical device. The disinfection structure 102 attaches to the track structure 101 such that the disinfection structure 102 moves along a path formed by the track structure 101. The disinfection structure 102 is a self propelled structure. By self propelled disinfection structure 102 is meant that the disinfection structure 102 generates the motive forces necessary to move the disinfection structure 102 along the path formed by the track structure 101. The disinfection structure 102 discharges a disinfection solution 136 directly onto the door 103 handle 104. The disinfection solution 136 is described elsewhere in this disclosure. The disinfection structure 102 comprises a housing 121, a propulsion circuit 122, and a control circuit 123. The housing 121 contains the propulsion circuit 122 and the control circuit 123.

The housing 121 is a rigid structure. The housing 121 contains the propulsion circuit 122 and the control circuit 123. The housing 121 is formed with all apertures and form factors necessary to allow the housing 121 to accommodate the use and operation of the invention 100. Methods to form a housing 121 suitable for the purposes described in this disclosure are well-known and documented in the mechanical arts. The housing 121 comprises a magnetic chamber 131, a reservoir 134 chamber 132, and a tracking wheel 133.

The magnetic chamber 131 is an enclosed space that is formed in the housing 121. The magnetic chamber 131 forms a protected space that encloses the propulsion circuit 122 and all the elements of the control circuit 123 with the exception of the pump 163. The magnetic chamber 131 is a fluid impermeable protected space that protects its contents from the disinfection solution 136 contained in the reservoir 134 chamber 132.

The reservoir 134 chamber 132 is an enclosed space that is formed in the housing 121. The reservoir 134 chamber 132 forms a protected space that encloses the reservoir 134, the spray nozzle 135, the disinfection solution 136, and the pump 163 of the control circuit 123. The reservoir 134 chamber 132 comprises a reservoir 134 and a spray nozzle 135.

The spray nozzle 135 is a nozzle that discharges the disinfection solution 136 under pressure directly onto the door 103 handle 104. The path formed by the guide track 111 is selected such that the discharge of the disinfection solution 136 through the spray nozzle 135 will fall on all the surfaces of the door 103 handle 104 as the housing 121 follows the path formed by the guide track 111. The spray nozzle 135 mounts in the housing 121 such that the spray of disinfection solution 136 that is discharged from the housing 121 is always directed towards the spray nozzle 135.

The reservoir 134 is a containment structure. The reservoir 134 stores the disinfection solution 136 that is subsequently used to disinfect the door 103 handle 104.

The disinfection solution 136 is a cleaning solution. The disinfection solution 136 is selected such that the disinfection solution 136 poisons the biochemical metabolic processes of pathogens on the door 103 handle 104. The disinfection solution 136 is selected such that direct contact of the disinfection solution 136 with the pathogens on the door 103 handle 104 is sufficient to poison the biochemical metabolic processes of pathogens. In the first potential embodiment of the disclosure, the disinfection solution 136 is selected from the group consisting of a water based quaternary ammonium CAS (8001-54-5) 241 solution and a water based sodium 3,5-dichloro-2,4,6-trioxy,1,3,5-triazinan-1-ide CAS (2893-78-9) 242 solution.

The quaternary ammonium (CAS 8001-54-5) 241 is a compound. The quaternary ammonium (CAS 8001-54-5) 241 is defined elsewhere in this disclosure. The quaternary ammonium (CAS 8001-54-5) 241 is a water soluble compound. The quaternary ammonium (CAS 8001-54-5) 241 is known as a pharmacologically active media with an ability to disrupt the biochemistry of microorganisms. The quaternary ammonium (CAS 8001-54-5) 241 is approved for use by the FDA for use against COVID-19.

The sodium 3,5-dichloro-2,4,6-trioxy,1,3,5-triazinan-1-ide (CAS 2893-78-9) 242 is a compound. The sodium 3,5-dichloro-2,4,6-trioxy,1,3,5-triazinan-1-ide (CAS 2893-78-9) 242 is defined elsewhere in this disclosure. The sodium 3,5-dichloro-2,4,6-trioxy,1,3,5-triazinan-1-ide (CAS 2893-78-9) 242 is a water soluble compound. The sodium 3,5-dichloro-2,4,6-trioxy,1,3,5-triazinan-1-ide (CAS 2893-78-9) 242 is known as a pharmacologically active media with an ability to disrupt the biochemistry of microorganisms. The sodium 3,5-dichloro-2,4,6-trioxy,1,3,5-triazinan-1-ide (CAS 2893-78-9) 242 is believed to be effective against the COVID-19 virus.

The applicant prefers the use of quaternary ammonium (CAS 8001-54-5) 241 in the first potential embodiment of the disclosure.

The tracking wheel 133 is a wheel that secures the housing 121 to the guide track 111 of the track structure 101. The tracking wheel 133 is sized such that the tracking wheel 133 inserts into the guide track 111. The tracking wheel 133 inserts into the guide track 111 such that the tracking wheel 133 rolls as the housing 121 moves along the path formed by the guide track 111.

The propulsion circuit 122 is an electric circuit. The propulsion circuit 122 generates a single alternating magnetic field. By alternating magnetic fields is meant that the field direction of the magnetic field generated by the propulsion circuit 122 changes between a first magnetic field direction and a second magnetic field direction wherein the second magnetic field direction is the reverse of the first magnetic field direction. The control circuit 123 controls the direction of the magnetic field generated by the propulsion circuit 122 such that the interaction between the magnetic field generated by the propulsion circuit 122 and the plurality of stationary magnets 114 generates a motive force that moves the disinfection structure 102 along the guide track 111 of the track structure 101. The propulsion circuit 122 comprises a plurality of transistors 141, an electromagnetic coil 142, a first pull-up resistor 151, and a second pull-up resistor 152. The plurality of transistors 141, the electromagnetic coil 142, the first pull-up resistor 151, and the second pull-up resistor 152 are electrically interconnected.

Each of the plurality of transistors 141 is a three terminal electric circuit element known as a transistor. The transistor is defined elsewhere in this disclosure. Each of the plurality of transistors 141 is used within the propulsion circuit 122 as an electrically controlled switch. The control circuit 123 controls the operation and the actuation of each of the plurality of transistors 141. Each of the plurality of transistors 141 performs a function selected from the group consisting of: a) enabling and disabling the operation of the propulsion circuit 122; and, b) determining the direction of motion of the housing 121 along the path formed by the guide track 111. The plurality of transistors 141 determines the direction of motion of the housing 121 along the path formed by the guide track 111 by controlling the direction of the flow of electricity through the electromagnetic coil 142. The plurality of transistors 141 comprises a first transistor 201, a second transistor 202, a third transistor 203, a fourth transistor 204, and a fifth transistor 205.

The electromagnetic coil 142 is an electromagnet. The electromagnetic coil 142 is an electrically operated device. The electromagnetic coil 142 generates the single alternating magnetic field produced by the propulsion circuit 122. The magnetic field produced by the propulsion circuit 122 is generated by passing an electric current through the electromagnetic coil 142. The direction of the field that is generated by the electromagnetic coil 142 is determined by the direction of the electric current flow through the electromagnetic coil 142. The electromagnetic coil 142 comprises a first lead 181 and a second lead 182.

The first lead 181 is a first electric termination of the electromagnetic coil 142. The first lead 181 receives an electric current from the second emitter 222 of the second transistor 202 when the first direction control signal 171 has a high voltage level. The first lead 181 discharges the electric current flowing through the electromagnetic coil 142 into the fifth collector 215 of the fifth transistor 205 when the second direction control signal 172 has a high voltage level. The second lead 182 is a second electric termination of the electromagnetic coil 142. The second lead 182 receives an electric current from the fourth collector 214 of the fourth transistor 204 when the second direction control signal 172 has a high voltage level. The second lead 182 discharges the electric current flowing through the electromagnetic coil 142 into the third collector 213 of the third transistor 203 when the first direction control signal 171 has a high voltage level.

The first transistor 201 is the transistor selected from the plurality of transistors 141 that controls the flow of electricity from the external power source 164 into both the second transistor 202 and the fourth transistor 204. The logic module 161 controls the operation of the first transistor 201 using the master control signal 173.

The second transistor 202 is the transistor selected from the plurality of transistors 141 that controls the flow of electricity from the first transistor 201 into the electromagnetic coil 142. The logic module 161 controls the operation of the second transistor 202 using the first direction control signal 171.

The third transistor 203 is the transistor selected from the plurality of transistors 141 that returns the flow of electricity from the electromagnetic coil 142 into the external power source 164. The logic module 161 controls the operation of the third transistor 203 using the first direction control signal 171.

The fourth transistor 204 is the transistor selected from the plurality of transistors 141 that controls the flow of electricity from the first transistor 201 into the electromagnetic coil 142. The logic module 161 controls the operation of the fourth transistor 204 using the second direction control signal 172.

The fifth transistor 205 is the transistor selected from the plurality of transistors 141 that returns the flow of electricity from the electromagnetic coil 142 into the external power source 164. The logic module 161 controls the operation of the fifth transistor 205 using the second direction control signal 172.

The first pull-up resistor 151 is an electric resistor. The first pull-up resistor 151 electrically connects in series between a first transistor 201 selected from the plurality of transistors 141 and a second transistor 202 selected from the plurality of transistors 141. The first pull-up resistor 151 limits the flow of electricity from the first transistor 201 through both the second transistor 202 and the electromagnetic coil 142. The second pull-up resistor 152 is an electric resistor. The second pull-up resistor 152 electrically connects in series between the first transistor 201 selected from the plurality of transistors 141 and a fourth transistor 204 selected from the plurality of transistors 141. The second pull-up resistor 152 limits the flow of electricity from the first transistor 201 through both the fourth transistor 204 and the electromagnetic coil 142.

The control circuit 123 is an electric circuit. The control circuit 123 controls the operation of the propulsion circuit 122. The control circuit 123 controls the direction of movement of the disinfection structure 102 along the guide track 111 of the track structure 101. The control circuit 123 controls the discharge of the disinfection solution 136 on the door 103 handle 104.

The control circuit 123 uses the plurality of transistors 141 to determine the direction of flow of the electric current through the electromagnetic coil 142 and thereby the magnetic field direction generated by the propulsion circuit 122. The control circuit 123 generates the motive forces necessary to move the disinfection structure 102 along the path formed by the guide track 111. The control circuit 123 generates these motive forces by changing the magnetic field direction of the magnetic field generated by the propulsion circuit 122. By changing the magnetic field generated by the electromagnetic coil 142, the control circuit 123 is able to change the interaction between the propulsion circuit 122 magnetic field and the magnetic field structure generated by the plurality of stationary magnets 114 to move the disinfection structure 102 along the guide track 111. This disclosure uses operating principles that are similar to the principles used in the operation of magnetically levitated trains.

The control circuit 123 comprises a logic module 161, a communication module 162, a pump 163, and an external power source 164. The logic module 161, the communication module 162, the pump 163, and the external power source 164 are electrically interconnected.

The logic module 161 is an electric circuit. The logic module 161 is a readily and commercially available programmable electronic device that is used to manage, regulate, and operate the disinfection structure 102.

Depending on the specific design and the selected components, the logic module 161 can be a separate component within the disinfection structure 102 or the functions of the logic module 161 can be incorporated into another component within the disinfection structure 102. The communication module 162 is a wireless electronic communication device that allows the logic module 161 to wirelessly communicate with a personal data device 191. Specifically, the communication module 162 establishes a wireless communication link 192 between the disinfection structure 102 and the personal data device 191. In the first potential embodiment of the disclosure, the communication module 162 supports a communication protocol selected from the group consisting of a WiFi™ protocol or a Bluetooth™ protocol.

The personal data device 191 is a programmable electrical device that provides data management and communication services through one or more functions referred to as an application 193. The application 193 is a set of logical operating instructions that are performed by the personal data device 191. The addition of an application 193 will provide increased functionality for the personal data device 191. This disclosure assumes that an application 193 exists for the purpose of interacting with the invention 100. Methods to design and implement an application 193 on a personal data device 191 are well known and documented in the electrical arts.

In the first potential embodiment of the disclosure, the personal data device 191: a) generates and transmits operating instructions for use by the logic module 161; and, b) receives and displays operational data from the logic module 161.

The logic module 161 further comprises a first direction control signal 171, a second direction control signal 172, a master control signal 173, and an inertial sensor 174. The logic module 161 controls the operation of the pump 163. The logic module 161 controls the operation of the first direction control signal 171. The logic module 161 controls the operation of the second direction control signal 172. The logic module 161 controls the operation of the master control signal 173. The logic module 161 monitors the inertial sensor 174. The logic module 161 adjusts the setting of the first direction control signal 171, the second direction control signal 172, and the master control signal 173 based on motions sensed by the inertial sensor 174.

The first direction control signal 171 is an electrical control signal that is generated by the logic module 161. The first direction control signal 171 is a binary signal that has a high voltage level and a low voltage level. The first direction control signal 171 electrically connects to the second transistor 202 and the third transistor 203. When the logic module 161 generates the first direction control signal 171, the logic module 161 configures the second transistor 202 and the third transistor 203 to pass an electric current through the electromagnetic coil 142 in a first direction.

The second direction control signal 172 is an electrical control signal that is generated by the logic module 161. The second direction control signal 172 is a binary signal that has a high voltage level and a low voltage level. The logic module 161 maintains the second direction control signal 172 at a high voltage level when the first direction control signal 171 is at a low voltage level. The logic module 161 maintains the second direction control signal 172 at a low voltage level when the first direction control signal 171 is at a high voltage level. The second direction control signal 172 electrically connects to the fourth transistor 204 and the fifth transistor 205. When the logic module 161 generates the second direction control signal 172, the logic module 161 configures the fourth transistor 204 and the fifth transistor 205 to pass an electric current through the electromagnetic coil 142 in a second direction that is opposite to the first direction.

The master control signal 173 is an electrical control signal that is generated by the logic module 161. The master control signal 173 is a binary signal that has a high voltage level and a low voltage level. The master control signal 173 controls the operation of the first transistor 201. The logic module 161 uses the first transistor 201 to enable and disable the operation of the propulsion circuit 122.

The inertial sensor 174 is an electric sensor. The inertial sensor 174 detects the opening of the door 103. The logic module 161 detects the opening of the door 103 using the inertial sensor 174. The logic module 161 operates under the assumption that the actuation of the inertial sensor 174 indicates that the door 103 handle 104 has been used to open the door 103 and that the door 103 handle 104 should be disinfected.

The pump 163 is an electrically powered device. The pump 163 is an electrically operated device. The pump 163 generates a pressure differential that transports the disinfection solution 136 from the reservoir 134 to the spray nozzle 135 for discharge. The logic module 161 controls the operation of the pump 163. The logic module 161 initiates the operation of the pump 163 when the master control signal 173 is used to actuate the switch function of the first transistor 201 of the plurality of transistors 141 to a closed position. The logic module 161 discontinues the operation of the pump 163 when the master control signal 173 is used to actuate the switch function of the first transistor 201 of the plurality of transistors 141 to an open position.

The external power source 164 is an externally provisioned source of electric energy. The external power source 164 provides the electric energy required to operate the propulsion circuit 122 and the control circuit 123 of the disinfection structure 102. The external power source 164 is defined elsewhere in this disclosure.

The first transistor 201 further comprises a first collector 211, a first emitter 221, and a first base 231. The second transistor 202 further comprises a second collector 212, a second emitter 222, and a second base 232. The third transistor 203 further comprises a third collector 213, a third emitter 223, and a third base 233. The fourth transistor 204 further comprises a fourth collector 214, a fourth emitter 224, and a fourth base 234. The fifth transistor 205 further comprises a fifth collector 215, a fifth emitter 225, and a fifth base 235.

The first collector 211 is the collector of the first transistor 201. The first collector 211 electrically connects to the external power source 164. The second collector 212 is the collector of the second transistor 202.

The second collector 212 electrically connects to the first pull-up resistor 151. The first pull-up resistor 151 forms an electrical connection between the first emitter 221 of the first transistor 201 and the second collector 212 such that the first pull-up resistor 151 can limit the flow of electricity into the second transistor 202. The third collector 213 is the collector of the third transistor 203. The third collector 213 electrically connects to the second lead 182 of the electromagnetic coil 142. The fourth collector 214 is the collector of the fourth transistor 204.

The fourth collector 214 electrically connects to the second pull-up resistor 152. The second pull-up resistor 152 forms an electrical connection between the first emitter 221 of the first transistor 201 and the fourth collector 214 such that the second pull-up resistor 152 can limit the flow of electricity into the fourth transistor 204. The fifth collector 215 is the collector of the third transistor 203. The fifth collector 215 electrically connects to the first lead 181 of the electromagnetic coil 142.

The first emitter 221 is the emitter of the first transistor 201. The first emitter 221 electrically connects to both the first pull-up resistor 151 and the second pull-up resistor 152. The second emitter 222 is the emitter of the second transistor 202. The second emitter 222 electrically connects to the first lead 181 of the electromagnetic coil 142. The third emitter 223 is the emitter of the third transistor 203. The third emitter 223 is the electric connection that returns the electricity flowing through the third transistor 203 to the external power source 164. The fourth emitter 224 is the emitter of the fourth transistor 204. The fourth emitter 224 electrically connects to the second lead 182 of the electromagnetic coil 142. The fifth emitter 225 is the emitter of the fifth transistor 205. The fifth emitter 225 is the electric connection that returns the electricity flowing through the third transistor 203 to the external power source 164.

The first base 231 is the base of the first transistor 201. The first base 231 electrically connects to the master control signal 173 generated by the logic module 161. The second base 232 is the base of the second transistor 202. The second base 232 electrically connects to the first direction control signal 171 generated by the logic module 161. The third base 233 is the base of the third transistor 203. The third base 233 electrically connects to the first direction control signal 171 generated by the logic module 161. The fourth base 234 is the base of the fourth transistor 204. The fourth base 234 electrically connects to the second direction control signal 172 generated by the logic module 161. The fifth base 235 is the base of the fifth transistor 205. The fifth base 235 electrically connects to the second direction control signal 172 generated by the logic module 161.

In the first potential embodiment of the disclosure, the intent of the applicant is to protect against a virus such as the COVID-19 virus. A virus is a microorganism. A virus comprises a nucleic acid and a protein shell. The protein shell forms a containment structure for the nucleic acid structure. In this disclosure, the virus is assumed to be a poison or, more specifically a toxin. The terms poison and toxin are described elsewhere in this disclosure. The virus is a biochemical structure that "infects" a host cell. By infecting a host cell is meant that the virus deposits the nucleic acid structure in the host cell such that the energy produced by the biochemical processes within the host cell is diverted towards the replication of the nucleic acid structure of the virus. An evolved virus refers to a virus that further comprises an envelope. The envelope is a lipid based structure that is similar to a cell membrane. The envelope encloses and protects the nucleic acid structure and the protein shell. The virus is defined elsewhere in this disclosure. The COVID-19 virus is defined in elsewhere in this disclosure.

The following definitions were used in this disclosure:

Activated Carbon: As used in this disclosure, activated carbon is a form of carbon that is processed in a manner that presents a large surface area for chemical interactions. The surface of activated carbon is used to adsorb chemical contaminants from a fluid flow that is passed through the activated carbon.

Adsorbtion: As used in this disclosure, adsorbtion refers to the formation of a layer of molecules on a surface.

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Ammonia: As used in this disclosure, ammonia (CAS 7664-41-7) refers to a chemical compound with the formula NH3. The chemical term ammonium (CAS 14789-03-9) refers to an ammonia molecule that has formed a hydrogen bond with a hydrogen ion. Ammonium has the chemical formula NH4+. The chemical quaternary ammonium (CAS 8001-54-5) refers to a chemical compound wherein the hydrogen elements of ammonium, including the hydrogen bonded hydrogen ion are replaced with other molecules or atoms (potentially including hydrogen). The FDA considers quaternary ammonium to be effective against SARs-like viruses including COVID-19.

Antigen: As used in this disclosure, an antigen is a substance that initiates an adaptive immune response within a living organism.

Application or App: As used in this disclosure, an application or app is a self-contained piece of software that is especially designed or downloaded for use with a personal data device.

Atmosphere: As used in this disclosure, the atmosphere refers to a blanket of gases (primarily nitrogen and oxygen) that surround the earth. Typical atmospheric conditions are approximated and characterized as the normal temperature and pressure. Atmospheric gases are commonly called air.

Bed Filter: As used in this disclosure, a bed filter comprises a particulate material through which a fluid is passed such that particulate material captures solids contained within the fluid while allowing the fluid itself to pass through the particulate matter.

Bimodal Flexible Structure: As used in this disclosure, a bimodal flexible structure is a structure that: a) responds to forces that are applied to one or more dimensional axes of the bimodal flexible structure in the manner of a rigid structure; while, b) simultaneously responding to forces that are applied to a dimensional axis that is perpendicular to the one or more dimensional axes described in (a) in the manner of a semi-rigid structure with an inelastic nature. A conduit structure is an example of a bimodal flexible structure. Specifically, a conduit structure acts as a rigid structure to forces that are applied in a radial direction towards the center axis of the prism structure of the conduit structure while being allowing the prism structure of the conduit to bend such that the conduit can be shaped into a non-Euclidean prism. A drafting spline is another example of a bimodal flexible structure. The resistance of a wire to compressive forces along the center axis of the wire allows a wire to behave as a bimodal flexible structure.

Biochemistry: As used in this disclosure, biochemistry refers to the chemical substances and the chemical processes associated with biological processes.

Bluetooth™: As used in this disclosure, Bluetooth™ is a standardized communication protocol that is used to wirelessly interconnect electronic devices.

Bulk Solid: As used in this disclosure, a bulk solid is a material that is formed from an accumulation of discrete particles. While the discrete particles of the bulk solid are solid materials, in aggregate the physical performance of bulk solid will exhibit fluid characteristics such as flow or taking the shape of a container.

CAS: As used in this disclosure, CAS refers to a CAS registry number, often called the CAS number. This CAS is a unique identification number that is assigned by the Chemical Abstract Services to a chemical compound. The Chemical Abstract Services maintains registry numbers in a database. The Chemical Abstract Services is a division of the American Chemical Society database. In this disclosure, when an identification mismatch occurs between the CAS and the name of a chemical substance, the CAS should be used.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Clean: As used in this disclosure, the term clean refers to an object without dirt, unwanted markings, or undesirable pathogens. When referring to a surface, the term clean can also refer to removing unwanted objects from the surface. The term cleaning refers to the action of making an object clean.

Cleaning Agent: As used in this disclosure, a cleaning agent is a chemical compound used to remove pathogens, dirt, and detritus from a surface.

Cleaning Solution: As used in this disclosure, a cleaning solution is a chemical solution that contains a solvent used to dissolve a cleaning agent.

Coil: As used in this disclosure, a coil is a structure that has the shape of a helix, volute, or a spiral. The structure of the coil is often a cord, wire, hose, or tube.

Communication Link: As used in this disclosure, a communication link refers to the structured exchange of data between two objects.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

COVID-19: As used in this disclosure, COVID-19 is a virus that is highly contagious between humans. The COVID-19 virus is also known as the severe acute respiratory syndrome coronavirus 2 (SARS-CoV-2). The COVID-19 is responsible for the COVID-19 pandemic of 2020. The COVID-19 is an evolved virus. The COVID-19 has a diameter a range of between 50 and 200 nanometers. This disclosure assumes that a representative diameter for COVID-19 is 100 nanometers. As of the writing of this definition, the environmental stability (the half-life survival time of the virus outside of the host) is between one and ten hours. COVID-19 structures appear to be susceptible to ultraviolet C radiation (specifically wavelengths of 260-265 nanometers).

Disinfectant: As used in this disclosure, a disinfectant is a chemical that destroys or inhibits the activities of pathogenic microorganisms.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Door: As used in this disclosure, a door is a movable or removable barrier that is attached to the wall of a room or the surface of a container for the purpose of allowing or preventing access through an aperture into the room or container.

Electromagnet: As used in this disclosure, an electromagnet is a core formed from a magnetic material that has a coil formed from an electric current carrying conductor wrapped around it. When an electric current flows through the coil, The core exhibits magnetic properties when an electric current flows through the coil and exhibits no (or reduced) magnetic properties when electric current is not flowing through the coil.

External Power Source: As used in this disclosure, an external power source is a source of the energy that is externally provided to enable the operation of the present disclosure. Examples of external power sources include, but are not limited to, electrical power sources (including batteries) and compressed air sources.

Filter: As used in this disclosure, a filter is a mechanical device that is used to separate solids that are suspended in a liquid or a gas. A strainer is type of filter with what would be considered a coarse mesh measurement.

Flexible: As used in this disclosure, flexible refers to an object or material that will deform when a force is applied to it but that will not necessarily return to its original shape when the deforming force is removed.

Flow: As used in this disclosure, a flow refers to the passage of a fluid past a fixed point. This definition considers bulk solid materials as capable of flow.

Fluid: As used in this disclosure, a fluid refers to a state of matter wherein the matter is capable of flow and takes the shape of a container it is placed within. The term fluid commonly refers to a liquid or a gas.

Fluidic Connection: As used in this disclosure, a fluidic connection refers to a tubular structure that transports a fluid from a first object to a second object. Methods to design and use a fluidic connections are well-known and documented in the mechanical, chemical, and plumbing arts.

Form Factor: As used in this disclosure, the term form factor refers to the size and shape of an object.

Gas: As used in this disclosure, a gas refers to a state (phase) of matter that is fluid and that fills the volume of the structure that contains it. Stated differently, the volume of a gas always equals the volume of its container.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Grip: As used in this disclosure, a grip is an accommodation formed on or within an object that allows the object to be grasped or manipulated by a hand.

Handle: As used in this disclosure, a handle is an object by which a tool, object, or door is held or manipulated with the hand.

Helix: As used in this disclosure, a helix is the three-dimensional structure that would be formed by a wire that is wound uniformly around the surface of a cylinder or a cone. If the wire is wrapped around a cylinder the helix is called a cylindrical helix. If the wire is wrapped around a cone, the helix is called a conical helix. A synonym for conical helix would be a volute. The helix has a right handed and left handed orientation. When viewed along the center axis of the helix, if the helix structure moves away from the observer along the clockwise direction, the helix is considered a right handed helix. If the helix structure moves towards the observer along the clockwise direction, the helix is considered a left handed helix. The handedness of the helix does not depend on the end of the helix being viewed. The helix is mathematically defined by the parametric equation set: $x(t)=\cos(t)$, $y(t)=\sin(t)$, and $z=t$.

HEPA: As used in this disclosure, a HEPA filter is a filter that meets standards set by the United States Department of Energy. The HEPA standard defines several classes of filters that are primarily differentiated by the percentage of 0.3 micrometer particles that the filter will remove from the air that passes through the filter. HEPA is an acronym that stands for high efficiency particulate arrestor.

Housing: As used in this disclosure, a housing is a rigid structure that encloses and protects one or more devices.

Inertia: As used in this disclosure, the term inertia describes an object that is not under the influence of an accelerating force. By under the influence is meant that the velocity of the object maintains a constant speed and direction (i.e. the object is not under acceleration or deceleration).

Inertial Sensor: As used in this disclosure, an inertial sensor is a form of a force sensor that measures the change in the inertia of an object.

Lead: As used in this disclosure, a lead is a conductor that is physically used to electrically connect an electrical component into a larger circuit assembly.

Liquid: As used in this disclosure, a liquid refers to a state (phase) of matter that is fluid and that maintains, for a given pressure, a fixed volume that is independent of the volume of the container.

Logic Circuit: As used in this disclosure, a logic circuit is electrical device that receives one or more digital or analog inputs and uses those digital or analog inputs to generate one or more digital or analog outputs. This disclosure allows, but does not assume, that the logic circuit is programmable.

Logic Module: As used in this disclosure, a logic module is a readily and commercially available electrical device that accepts digital and analog inputs, processes the digital and analog inputs according to previously specified logical processes and provides the results of these previously specified logical processes as digital or analog outputs. The disclosure allows, but does not assume, that the logic module is programmable.

Magnet: As used in this disclosure, a magnet is an ore, alloy, or other material that has its component atoms arranged so the material exhibits properties of magnetism such as: 1) attracting other iron-containing objects; 2) attracting other magnets; or, 3) or aligning itself in an external magnetic field. A magnet is further defined with a north pole and a south pole. By aligning with an external magnetic field is meant that the north-south pole structure of a first magnet will align with the north south pole of a second magnet. The pole of any first magnet will attract the opposite pole of any second magnet (i.e. a north pole will attract a south pole).

Magnetic Material: As used in this disclosure, a magnetic material is a substance that attracts or is attracted to a magnet but that itself has no net magnetic moment (beyond any residual moment created by prior use). Common classes of magnetic materials include ferromagnetic, diamagnetic, paramagnetic, ferrimagnetic and antiferromagnetic.

Metabolism: As used in this disclosure, metabolism refers to the chemical processes that occur within a living cell.

Microorganism: As used in this disclosure, a microorganism is an organism too small to be viewed by the unaided eye. Microorganisms are typically single celled organisms such as bacteria, yeast, viruses, protozoa, fungi and algae. A pathogen refers to a microorganism that has the potential to cause illness or disease.

N95 Filter: As used in this disclosure, an N95 filter is a surface filter designed to remove particulates from an air flow. The established performance standard for the N95 filter requires that the N95 filter be capable of removing 95% of the particulates having a diameter of greater than or equal to 300 nanometers from the air flow. As a practical matter, most N95 filters remove over 99% (a published estimate that was current as this definition is written has 99.8%) of the particulates having a diameter of greater than or equal to 100 nanometers from the air flow. An N95 respirator, or less formally an N95 mask, is a respirator that filters the flow of breathing air through an N95 filter. An N99 filter is rated as removing over 99% of the particulates having a diameter of greater than or equal to 300 nanometers from the air flow.

Negative Space: As used in this disclosure, negative space is a method of defining an object through the use of open or empty space as the definition of the object itself, or, through the use of open or empty space to describe the boundaries of an object.

Non-Euclidean Prism: As used in this disclosure, a non-Euclidean prism is a prism structure wherein the center axis of the prism lies on a non-Euclidean plane or is otherwise formed with a curvature.

Non-Polar Molecule: As used in this disclosure, a non-polar molecule refers to a molecular structure that: a) is electrically neutral; and, b) has a uniform spatial distribution of the electrons within the molecule.

Nozzle: As used in this disclosure, a nozzle is a device that receives fluid under pressure and releases the fluid in a controlled manner into an environment.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Pan: As used in this disclosure, a pan is a hollow and prism-shaped containment structure. The pan has a single open face. The open face of the pan is often, but not always, the superior face of the pan. The open face is a surface selected from the group consisting of: a) a congruent end of the prism structure that forms the pan; and, b) a lateral face of the prism structure that forms the pan. A semi-enclosed pan refers to a pan wherein the closed end of prism structure of the pan and/or a portion of the closed lateral faces of the pan is are open.

PDD: As used in this disclosure, PDD is an acronym for personal data device.

Personal Data Device: As used in this disclosure, a personal data device is a handheld logical device that is used for managing personal information and communication. Examples of personal data device include, but are not limited to, cellular phones, tablets, and smartphones. See logical device Perimeter: As used in this disclosure, a perimeter is one or more curved or straight lines that bounds an enclosed area on a plane or surface. The perimeter of a circle is commonly referred to as a circumference.

Permeate: As used in this disclosure, to permeate means to mix or apply a chemical compound into an object such that the compound is diffused or distributed throughout the structure. The chemical sense of the term impregnate is a synonym for permeate.

Pharmacologically Active Media: As used in this disclosure, a pharmacologically active media refers to a chemical substance that has a biochemical or physiological effect on a biological organism.

Phase: As used in this disclosure, phase refers to the state of the form of matter. The common states of matter are solid, liquid, gas, and plasma.

Plasma: As used in this disclosure, plasma refers to a state (phase) of matter wherein the outer valence electrons of an atom (or molecule) have been separated from their nucleus but remain with the matter. A plasma is an electrically neutral state of matter that is formed from the ions of the separated atoms. Plasmas generally, but not necessarily behaves like a gas in that a plasma fills the volume of the structure that contains it.

Poison: As used in this disclosure, a poison is a chemical substance that interferes with the normal biological processes of a biological organism. The term poison often implies the injury to or death of the biological organism. A toxin is a poison that generates an immune system response.

Polar Molecule: As used in this disclosure, a polar molecule refers to a molecular structure that: a) is electrically neutral; but, b) does not have a uniform spatial distribution of the electrons within the molecule. A polar molecule will present one or more electrically positive poles and the same number of electrically negative poles within the molecular structure.

Polarity: As used in this disclosure, the term polarity is used to describe a physical property or physical characteristic wherein: 1) the physical property or physical characteristic manifests two opposing attributes, tendencies, characteristics, or principals; and, 2) the two opposing attributes, tendencies, characteristics, or principals have an intrinsic separation, alignment, or orientation.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Pull-Up Resistor: As used in this disclosure, a pull-up resistor is an electrical resistor that is used to: 1) limit the current flow through a switching device; and, 2) to control the voltage level presented across a switch, a load resistor, or a pull-down resistor.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Radiation: As used in this disclosure, radiation refers to the discharge of energy from an object. The term is often applied to energy in the form of: a) waves, such as electromagnetic radiation or acoustic energy; b) nuclear radiation such as alpha, beta, and gamma, particle radiation; and, c) gravitational waves. The radiation of electromagnetic waves is often classified by the wavelength of the generated waves, such as ultraviolet and infrared radiation. See Wave Reservoir: As used in this disclosure, a reservoir refers to a container or containment system that is configured to store a liquid.

Resistance: As used in this disclosure, resistance refers to the opposition provided by an electrical circuit (or circuit element) to the electrical current created by a DC voltage is presented across the electrical circuit (or circuit element). The term impedance is often used for resistance when referring to an AC voltage that is presented across the electrical circuit (or circuit element).

Resistor: As used in this disclosure, a resistor is a well-known and commonly available electrical device that presents a resistance that inhibits the flow of electricity through an electric circuit. Within an electric circuit processing alternating currents, the resistor will not affect the phase of the alternating current. A current flowing through a resistor will create a voltage across the terminals of the resistor.

Rigid Structure: As used in this disclosure, a rigid structure is a solid structure formed from an inelastic material that resists changes in shape. A rigid structure will permanently deform as it fails under a force. See bimodal flexible structure.

Roll: As used in this disclosure, the term roll refers to the rotation of an object around an axis or center of rotation. The term roll is often used in the context of the motion of an object that is facilitated by the rotation of one or more wheels or a casters.

Semi-Enclosed Prism: As used in this disclosure, a semi-enclosed prism is a prism-shaped structure wherein a portion of the lateral face of the prism-shaped is removed or otherwise replaced with a negative space. Always use negative space.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Sodium Dichloroisocyanurate: As used in this disclosure, sodium dichloroisocyanurate is a commonly used name for sodium 3,5-dichloro-2,4,6-trioxy,1,3,5-triazinan-1-ide (CAS 2893-78-9). Sodium dichloroisocyanurate is a commonly used disinfecting agent that is available in a powder form. Sodium dichloroisocyanurate is soluble in water and alcohol. Sodium dichloroisocyanurate is also available in a dihydride formulation (sodium dichloroisocyanurate hydride CAS: 51580-86-0). Sodium dichloroisocyanurate is soluble in water at concentrations of over 200 grams per liter.

Solid: As used in this disclosure, a solid refers to a state (phase) of matter that: 1) has a fixed volume; and, 2) does not flow.

Solution: As used in this disclosure, a solution is a uniform mixture of two or more compounds in a liquid phase. The major component selected from the two or more compounds that forms the solution is called the solvent. The components remaining in the two or more compounds are called the solute. A polar solvent is a solvent formed from polar molecules. A non-polar solvent is a solvent formed from non-polar molecules. The rule of thumb that "like dissolves like" states that: a) solutes formed from polar molecules will dissolve in polar solvents but will not dissolve in non-polar solvents; and, b) solutes formed from non-polar molecules will dissolve in non-polar solvents but will not dissolve in polar solvents.

Spectrum: As used in this disclosure, a spectrum refers to the distribution and amplitude of the component frequencies of a source of electromagnetic radiation. Spectrums are typically organized and displayed by frequency or frequency range.

Spray: As used in this disclosure, a spray is a plurality of liquid drops dispersed in a gas.

Spray Nozzle: As used in this disclosure, a spray nozzle is a device that receives liquid under pressure and disperses that liquid into the atmosphere as a spray.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Track: As used in this disclosure, a track is a physical structural relationship between a first object and a second object that serves a purpose selected from the group consisting of: 1) fastening the second object to the first object; 2) controlling the path of motion of the first object relative to the second object in at least one dimension and in a maximum of two dimensions; or, 3) a combination of the first two elements of this group.

Transistor: As used in this disclosure, a transistor is a general term for a three terminal semiconducting electrical device that is used for electrical signal amplification and electrical switching applications. There are several designs of transistors. A common example of a transistor is an NPN transistor that further comprises a collector terminal, an emitter terminal, and a base terminal and which consists of a combination of two rectifying junctions (a diode is an example of a rectifying junction). Current flowing from the collector terminal through the emitter terminal crosses the two rectifier junctions. The amount of the electric current crossing the two rectified junctions is controlled by the amount of electric current that flows through the base terminal. This disclosure assumes the use of an NPN transistor. This assumption is made solely for the purposes of simplicity and clarity of exposition. Those skilled in the electrical arts will recognize that other types of transistors, including but not limited to, field effect transistors and PNP transistors, can be substituted for an NPN transistor without undue experimentation.

U-Shaped Structure: As used in this disclosure, a U-shaped structure refers to a three-sided structure comprising a crossbeam, a first arm, and a second arm. In a U-shaped structure, the first arm and the second arm project away from the crossbeam: 1) in the same direction; 2) at a roughly perpendicular angle to the crossbeam, and, 3) the span of the length of the first arm roughly equals the span of the length of the second arm. The first arm and the second arm project away from the crossbeam in the manner of a cantilever. An illiterate U-shaped structure is a U-shaped structure where the span of the length of the first arm does not equal the span of the length of the second arm.

Ultraviolet C Light: As used in this disclosure, ultraviolet C light is understood to be ultraviolet light with wavelengths in the range of 200 nm to 300 nm. Ultraviolet C light is considered to be the most effective light for disinfection. Within the ultraviolet C range, the most effective disinfection is considered to occur with radiation wavelengths between 248 nm and 262 nm.

Ultraviolet Light: As used in this disclosure, ultraviolet light is understood to be electromagnetic radiation with a wavelength lesser than visible light. In general usage, ultraviolet light is taken to mean electromagnetic radiation with a wavelength less than 400 nm. See ultraviolet radiation for a more specific definition.

Ultraviolet Radiation: As used in this disclosure, ultraviolet radiation refers to electromagnetic radiation with a wavelength in the approximate range of 400 nanometers to 10 nanometers. Ultraviolet has sub-classifications known as UVA, UVB, and UVC. UVA refers to ultraviolet light with a wavelength in the range of 315 nanometers and 400 nanometers. UVB refers to ultraviolet light with a wavelength in the range of 280 nanometers and 315 nanometers. UVC refers to ultraviolet light with a wavelength in the range 10 nanometers and 280 nanometers.

UV: As used in this disclosure, UV is an abbreviation for ultraviolet.

Vcc: As used in this disclosure, Vcc is an acronym for Voltage at the Common Collector. Technically, the Vcc is the primary power source for an NPN transistor. In this disclosure, the definition of Vcc is more broadly defined to mean a direct current voltage source.

Virus: As used in this disclosure, a virus is a biological entity that is capable of reproduction but does not have the biological mechanisms to generate the energy for replication. A virus "infects" a host cell and uses the biochemical biological processes of the host cell as the energy source that allows the virus to replicate. Because the virus is incapable of independently generating the biochemical energy necessary for reproduction, the traditional view is that viruses are not a form of life. All viruses comprise a nucleic acid structure and a protein shell. The nucleic acid structure is genetic material that is selected from the group consisting of RNA and DNA. The nucleic acid structure is enclosed within the protein shell. The protein shell is known as the capsid. The proteins of the capsid are encoded by the nucleic acid structure. The capsid: a) protects the nucleic acid structure when the virus is dormant; and, b) attaches the virus to a biological structure of a host cell that is suitable to support the replication of the virus. More evolved viruses further comprise an envelope. The envelope is a lipid based structure that is similar to a cell membrane. By similar to the cell membrane is meant that: a) the envelope is formed with a bilayer lipid structure similar to a cell membrane; and, b) the envelope will display membrane protein structures to its environment in a similar to a cell membrane. The envelope encloses the capsid and the nucleic acid structure. In this disclosure, a virus formed with an envelope is referred to as an evolved virus. The term virus can refer to viruses with or without an envelope.

Wave: As used in this disclosure, a wave is a mechanism capable of transferring energy without transferring mass. Specifically, a wave refers to a transfer of momentum or energy through an object or medium such that there is no significant change in the relative positions of the particles (or molecules) that make up the object or medium.

Wheel: As used in this disclosure, a wheel is a circular object that revolves around an axle or an axis and is fixed below an object to enable it to move easily over the ground. For the purpose of this disclosure, it is assumed that a wheel can only revolve in a forward and a backward direction. Wheels are often further defined with a rim and spokes. Spokes are also commonly referred to as a wheel disk.

WiFi™: As used in this disclosure, WiFi™ refers to the physical implementation of a collection of wireless electronic communication standards commonly referred to as IEEE 802.11x.

Wireless: As used in this disclosure, wireless is an adjective that is used to describe a communication channel between two devices that does not require the use of physical cabling.

With respect to the above description, it is to be realized that the optimum dimensional relationship for the various components of the invention described above and in FIGS. 1 through 9 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:
1. A door handle sanitizer comprising
a track structure and a disinfection structure;
wherein the track structure attaches the disinfection structure to the door;
wherein the door handle sanitizer is an electromechanical device;

wherein the door handle sanitizer is configured for use in spraying a disinfection solution onto a door handle of a door;

wherein the track structure is a flexible structure that forms a path that guides the disinfection structure around the door handle;

wherein the disinfection structure moves along the path formed by the track structure such that the disinfection structure has access to all surfaces of the door handle.

2. The door handle sanitizer according to claim 1 wherein the track structure is a mechanical structure;

wherein the track structure secures the disinfection structure to the door;

wherein the track structure is a bimodal flexible structure;

wherein the bimodal flexible structure of the track structure allows for the attachment of the track structure to the door with a curvature that allows the track structure to enclose or partially enclose the door handle;

wherein the track structure forms a track that guides the disinfection structure around the path that encloses or partially encloses the door handle;

wherein the path formed by the track structure provides the disinfection structure with the access required to discharge the disinfection solution directly onto all the surfaces of the door handle;

wherein the track structure is a passive magnetic structure;

wherein the magnetic structure of the track structure is aligned such that the track structure supports an active magnetic propulsion structure formed by the disinfection structure.

3. The door handle sanitizer according to claim 2 wherein the disinfection structure is an electromechanical device;

wherein the disinfection structure attaches to the track structure such that the disinfection structure moves along a path formed by the track structure;

wherein the disinfection structure is a self propelled structure;

wherein by self propelled disinfection structure is meant that the disinfection structure generates the motive forces necessary to move the disinfection structure along the path formed by the track structure;

wherein the disinfection structure discharges a disinfection solution directly onto the door handle.

4. The door handle sanitizer according to claim 3 wherein the track structure comprises a guide track, a magnet plate, a plurality of termination caps, and a plurality of stationary magnets;

wherein the plurality of stationary magnets attach to the magnet plate;

wherein the magnet plate and the plurality of termination caps attach to the guide track.

5. The door handle sanitizer according to claim 4 wherein the disinfection structure comprises a housing, a propulsion circuit, and a control circuit;

wherein the housing contains the propulsion circuit and the control circuit.

6. The door handle sanitizer according to claim 5 wherein the guide track is a track;

wherein the guide track forms a negative space with a semi-enclosed non-Euclidean structure;

wherein the guide track is sized to receive the tracking wheel of the disinfection structure such that the guide track guides the motion of the tracking wheel;

wherein the guide track is a bimodal flexible structure;

wherein the bimodal flexible structure of the guide track allows for the attachment of the guide track to the door with a curvature that allows the guide track to enclose or partially enclose the door handle;

wherein the guide track forms a track that guides the disinfection structure around the path that encloses or partially encloses the door handle.

7. The door handle sanitizer according to claim 6 wherein the magnet plate is a flexible disk-shaped structure;

wherein the magnet plate is a bimodal flexible structure;

wherein the bimodal flexible structure of the magnet plate allows for the attachment of the magnet plate to the door with a curvature that allows the magnet plate to enclose or partially enclose the door handle;

wherein the magnet plate attaches to the guide track such that the congruent ends of the disk structure of the magnet plate bends to follow the center axis of the non-Euclidean structure of the guide track;

wherein each of the plurality of stationary magnets attaches to a congruent end of the disk structure of the magnet plate.

8. The door handle sanitizer according to claim 7 wherein each of the plurality of termination caps is a bracing structure that attaches to a congruent end of the non-Euclidean structure of the guide track;

wherein the plurality of termination caps forms a blocking structure that prevents the disinfection structure from moving beyond the path formed by the guide track.

9. The door handle sanitizer according to claim 8 wherein each of the plurality of stationary magnets is a permanent magnet;

wherein the plurality of stationary magnets are arranged on the magnet plate such that the plurality of stationary magnets forms a plurality of alternating magnetic fields;

wherein by alternating magnetic fields is meant that any field directions of the magnetic fields generated by any two adjacent stationary magnets are reversed relative to each other;

wherein the plurality of stationary magnets forms a passive magnetic field structure that interacts with an active magnetic field structure formed by the disinfection structure to generate the motive forces necessary to move the disinfection structure along the path formed by the guide track.

10. The door handle sanitizer according to claim 9 wherein the housing is a rigid structure;

wherein the housing contains the propulsion circuit and the control circuit;

wherein the housing comprises a magnetic chamber, a reservoir chamber, and a tracking wheel;

wherein the magnetic chamber is an enclosed space that is formed in the housing;

wherein the magnetic chamber forms a protected space that encloses the propulsion circuit and all the elements of the control circuit with the exception of the pump;

wherein the reservoir chamber is an enclosed space that is formed in the housing;

wherein the reservoir chamber forms a protected space that encloses the reservoir, the spray nozzle, the disinfection solution, and the pump of the control circuit;

wherein the magnetic chamber is a fluid impermeable protected space that protects its contents from the disinfection solution contained in the reservoir chamber.

11. The door handle sanitizer according to claim 10
wherein the reservoir chamber comprises a reservoir and a spray nozzle;
wherein the spray nozzle is a nozzle that discharges the disinfection solution under pressure directly onto the door handle;
wherein the path formed by the guide track is selected such that the discharge of the disinfection solution through the spray nozzle will fall on all the surfaces of the door handle as the housing follows the path formed by the guide track;
wherein the spray nozzle mounts in the housing such that the spray of disinfection solution that is discharged from the housing is always directed towards the spray nozzle;
wherein the reservoir is a containment structure;
wherein the reservoir stores the disinfection solution that is subsequently used to disinfect the door handle;
wherein the disinfection solution is a cleaning solution;
wherein the disinfection solution is selected such that the disinfection solution poisons the biochemical metabolic processes of pathogens on the door handle;
wherein the disinfection solution is selected such that direct contact of the disinfection solution with the pathogens on the door handle is sufficient to poison the biochemical metabolic processes of pathogens;
wherein the disinfection solution is selected from the group consisting of a water based quaternary ammonium (CAS 8001-54-5) solution and a water based sodium 3,5-dichloro-2,4,6-trioxy,1,3,5-triazinan-1-ide (CAS 2893-78-9) solution.

12. The door handle sanitizer according to claim 11
wherein the tracking wheel is a wheel that secures the housing to the guide track of the track structure;
wherein the tracking wheel is sized such that the tracking wheel inserts into the guide track;
wherein the tracking wheel inserts into the guide track such that the tracking wheel rolls as the housing moves along the path formed by the guide track.

13. The door handle sanitizer according to claim 12
wherein the propulsion circuit is an electric circuit;
wherein the propulsion circuit generates a single alternating magnetic field;
wherein by alternating magnetic fields is meant that the field direction of the magnetic field generated by the propulsion circuit changes between a first magnetic field direction and a second magnetic field direction wherein the second magnetic field direction is the reverse of the first magnetic field direction;
wherein the control circuit controls the direction of the magnetic field generated by the propulsion circuit such that the interaction between the magnetic field generated by the propulsion circuit and the plurality of stationary magnets generates a motive force that moves the disinfection structure along the guide track of the track structure;
wherein the control circuit is an electric circuit;
wherein the control circuit controls the operation of the propulsion circuit;
wherein the control circuit controls the direction of movement of the disinfection structure along the guide track of the track structure;
wherein the control circuit controls the discharge of the disinfection solution on the door handle;
wherein the control circuit uses the plurality of transistors to determine the direction of flow of the electric current through the electromagnetic coil and thereby the magnetic field direction generated by the propulsion circuit;
wherein the control circuit generates the motive forces necessary to move the disinfection structure along the path formed by the guide track;
wherein the control circuit generates these motive forces by changing the magnetic field direction of the magnetic field generated by the propulsion circuit.

14. The door handle sanitizer according to claim 13
wherein the propulsion circuit comprises a plurality of transistors, an electromagnetic coil, a first pull-up resistor, and a second pull-up resistor;
wherein the plurality of transistors, the electromagnetic coil, the first pull-up resistor, and the second pull-up resistor are electrically interconnected;
wherein the control circuit comprises a logic module, a communication module, a pump, and an external power source;
wherein the logic module, the communication module, the pump, and the external power source are electrically interconnected.

15. The door handle sanitizer according to claim 14
wherein each of the plurality of transistors is a three terminal electric circuit element known as a transistor;
wherein each of the plurality of transistors is used within the propulsion circuit as an electrically controlled switch;
wherein the control circuit controls the operation and the actuation of each of the plurality of transistors;
wherein each of the plurality of transistors performs a function selected from the group consisting of: a) enabling and disabling the operation of the propulsion circuit; and, b) determining the direction of motion of the housing along the path formed by the guide track;
wherein the plurality of transistors determines the direction of motion of the housing along the path formed by the guide track by controlling the direction of the flow of electricity through the electromagnetic coil;
wherein the electromagnetic coil is an electromagnet;
wherein the electromagnetic coil is an electrically operated device;
wherein the electromagnetic coil generates the single alternating magnetic field produced by the propulsion circuit;
wherein the magnetic field produced by the propulsion circuit is generated by passing an electric current through the electromagnetic coil;
wherein the direction of the field that is generated by the electromagnetic coil is determined by the direction of the electric current flow through the electromagnetic coil;
wherein the electromagnetic coil comprises a first lead and a second lead;
wherein the first lead is a first electric termination of the electromagnetic coil;
wherein the second lead is a second electric termination of the electromagnetic coil.

16. The door handle sanitizer according to claim 15
wherein the logic module is an electric circuit;
wherein the communication module is a wireless electronic communication device that allows the logic module to wirelessly communicate with a personal data device;
wherein specifically, the communication module establishes a wireless communication link between the disinfection structure and the personal data device;

wherein the personal data device is a programmable electrical device;
wherein the personal data device: a) generates and transmits operating instructions for use by the logic module; and, b) receives and displays operational data from the logic module.

17. The door handle sanitizer according to claim 16
wherein the plurality of transistors comprises a first transistor, a second transistor, a third transistor, a fourth transistor, and a fifth transistor;
wherein the first transistor is the transistor selected from the plurality of transistors that controls the flow of electricity from the external power source into both the second transistor and the fourth transistor;
wherein the logic module controls the operation of the first transistor;
wherein the second transistor is the transistor selected from the plurality of transistors that controls the flow of electricity from the first transistor into the electromagnetic coil;
wherein the logic module controls the operation of the second transistor;
wherein the third transistor is the transistor selected from the plurality of transistors that returns the flow of electricity from the electromagnetic coil into the external power source;
wherein the logic module controls the operation of the third transistor;
wherein the fourth transistor is the transistor selected from the plurality of transistors that controls the flow of electricity from the first transistor into the electromagnetic coil;
wherein the logic module controls the operation of the fourth transistor;
wherein the fifth transistor is the transistor selected from the plurality of transistors that returns the flow of electricity from the electromagnetic coil into the external power source;
wherein the logic module controls the operation of the fifth transistor;
wherein the first pull-up resistor is an electric resistor;
wherein the first pull-up resistor electrically connects in series between a first transistor selected from the plurality of transistors and a second transistor selected from the plurality of transistors;
wherein the first pull-up resistor limits the flow of electricity from the first transistor through both the second transistor and the electromagnetic coil;
wherein the second pull-up resistor is an electric resistor;
wherein the second pull-up resistor electrically connects in series between the first transistor selected from the plurality of transistors and a fourth transistor selected from the plurality of transistors;
wherein the second pull-up resistor limits the flow of electricity from the first transistor through both the fourth transistor and the electromagnetic coil.

18. The door handle sanitizer according to claim 17
wherein the logic module further comprises a first direction control signal, a second direction control signal, a master control signal, and an inertial sensor;
wherein the logic module controls the operation of the pump;
wherein the logic module controls the operation of the first direction control signal;
wherein the logic module controls the operation of the second direction control signal;
wherein the logic module controls the operation of the master control signal;
wherein the logic module monitors the inertial sensor;
wherein the logic module adjusts the setting of the first direction control signal, the second direction control signal, and the master control signal based on motions sensed by the inertial sensor;
wherein the first direction control signal is an electrical control signal that is generated by the logic module;
wherein the first direction control signal is a binary signal that has a high voltage level and a low voltage level;
wherein the first direction control signal electrically connects to the second transistor and the third transistor;
wherein when the logic module generates the first direction control signal, the logic module configures the second transistor and the third transistor to pass an electric current through the electromagnetic coil in a first direction;
wherein the second direction control signal is an electrical control signal that is generated by the logic module;
wherein the second direction control signal is a binary signal that has a high voltage level and a low voltage level;
wherein the logic module maintains the second direction control signal at a high voltage level when the first direction control signal is at a low voltage level;
wherein the logic module maintains the second direction control signal at a low voltage level when the first direction control signal is at a high voltage level;
wherein the second direction control signal electrically connects to the fourth transistor and the fifth transistor;
wherein when the logic module generates the second direction control signal, the logic module configures the fourth transistor and the fifth transistor to pass an electric current through the electromagnetic coil in a second direction that is opposite to the first direction;
wherein the master control signal is an electrical control signal that is generated by the logic module;
wherein the master control signal is a binary signal that has a high voltage level and a low voltage level;
wherein the master control signal controls the operation of the first transistor;
wherein the logic module uses the first transistor to enable and disable the operation of the propulsion circuit;
wherein the inertial sensor is an electric sensor;
wherein the inertial sensor detects the opening of the door;
wherein the logic module detects the opening of the door using the inertial sensor;
wherein the logic module operates under the assumption that the actuation of the inertial sensor indicates that the door handle has been used to open the door and that the door handle should be disinfected.

19. The door handle sanitizer according to claim 18
wherein the pump is an electrically powered device;
wherein the pump is an electrically operated device;
wherein the pump generates a pressure differential that transports the disinfection solution from the reservoir to the spray nozzle for discharge;
wherein the logic module controls the operation of the pump;
wherein the logic module initiates the operation of the pump when the master control signal is used to actuate the switch function of the first transistor of the plurality of transistors to a closed position;
wherein the logic module discontinues the operation of the pump when the master control signal is used to actuate the switch function of the first transistor of the plurality of transistors to an open position.

20. The door handle sanitizer according to claim 19
wherein the first transistor further comprises a first collector, a first emitter, and a first base;
wherein the second transistor further comprises a second collector, a second emitter, and a second base;
wherein the third transistor further comprises a third collector, a third emitter, and a third base;
wherein the fourth transistor further comprises a fourth collector, a fourth emitter, and a fourth base;
wherein the fifth transistor further comprises a fifth collector, a fifth emitter, and a fifth base;
wherein the first collector is the collector of the first transistor;
wherein the first collector electrically connects to the external power source;
wherein the second collector is the collector of the second transistor;
wherein the second collector electrically connects to the first pull-up resistor;
wherein the first pull-up resistor forms an electrical connection between the first emitter of the first transistor and the second collector such that the first pull-up resistor can limit the flow of electricity into the second transistor;
wherein the third collector is the collector of the third transistor;
wherein the third collector electrically connects to the second lead of the electromagnetic coil;
wherein the fourth collector is the collector of the fourth transistor;
wherein the fourth collector electrically connects to the second pull-up resistor;
wherein the second pull-up resistor forms an electrical connection between the first emitter of the first transistor and the fourth collector such that the second pull-up resistor can limit the flow of electricity into the fourth transistor;
wherein the fifth collector is the collector of the third transistor;
wherein the fifth collector electrically connects to the first lead of the electromagnetic coil;
wherein the first emitter is the emitter of the first transistor;
wherein the first emitter electrically connects to both the first pull-up resistor and the second pull-up resistor;
wherein the second emitter is the emitter of the second transistor;
wherein the second emitter electrically connects to the first lead of the electromagnetic coil;
wherein the third emitter is the emitter of the third transistor;
wherein the third emitter is the electric connection that returns the electricity flowing through the third transistor to the external power source;
wherein the fourth emitter is the emitter of the fourth transistor;
wherein the fourth emitter electrically connects to the second lead of the electromagnetic coil;
wherein the fifth emitter is the emitter of the fifth transistor;
wherein the fifth emitter is the electric connection that returns the electricity flowing through the third transistor to the external power source;
wherein the first base is the base of the first transistor;
wherein the first base electrically connects to the master control signal generated by the logic module;
wherein the second base is the base of the second transistor;
wherein the second base electrically connects to the first direction control signal generated by the logic module;
wherein the third base is the base of the third transistor;
wherein the third base electrically connects to the first direction control signal generated by the logic module;
wherein the fourth base is the base of the fourth transistor;
wherein the fourth base electrically connects to the second direction control signal generated by the logic module;
wherein the fifth base is the base of the fifth transistor;
wherein the fifth base electrically connects to the second direction control signal generated by the logic module;
wherein the first lead receives an electric current from the second emitter of the second transistor when the first direction control signal has a high voltage level;
wherein the first lead discharges the electric current flowing through the electromagnetic coil into the fifth collector of the fifth transistor when the second direction control signal has a high voltage level;
wherein the second lead receives an electric current from the fourth collector of the fourth transistor when the second direction control signal has a high voltage level;
wherein the second lead discharges the electric current flowing through the electromagnetic coil into the third collector of the third transistor when the first direction control signal has a high voltage level.

* * * * *